United States Patent
Wortman et al.

(10) Patent No.: US 6,319,214 B1
(45) Date of Patent: Nov. 20, 2001

(54) VALVE-LESS FLUID CONTROL CIRCUIT FOR RHYTHMIC ACTION DEVICES

(75) Inventors: Donald E. Wortman, Rockville; John D. Bruno, Bowie, both of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/654,838

(22) Filed: Sep. 1, 2000

(51) Int. Cl.$^7$ ........................................... F15C 1/12
(52) U.S. Cl. ..................... 601/150; 601/158; 137/809; 137/814
(58) Field of Search ..................... 601/148–152; 137/806, 808, 812, 814, 809, 810

(56) References Cited

U.S. PATENT DOCUMENTS

| | | | |
|---|---|---|---|
| 3,350,008 | * 10/1967 | Avery | 137/821 |
| 3,467,125 | * 9/1969 | Dexter | 137/821 |
| 3,587,568 | * 6/1971 | Thomas | 128/33 |
| 3,643,351 | * 2/1972 | Eckerlin et al. | 36/2.5 |
| 5,109,832 | * 5/1992 | Proctor et al. | 128/24 |

* cited by examiner

*Primary Examiner*—Justine R. Yu
(74) *Attorney, Agent, or Firm*—Paul S. Clohan, Jr.

(57) ABSTRACT

A valve-less fluid control circuit for controlling rhythmic action devices, such as circulatory assist devices. The fluid control circuit has a plurality of pressure sensitive fluid oscillators for circulating a fluid. Each fluid oscillator includes a capacitance chamber unit for peristaltic pumping of fluid after being filled via an input conduit and a resistance conduit. A first control conduit provides an outlet of fluid from the capacitance unit during peristaltic pumping, and when the pressure of the fluid in the first control conduit reaches a certain level relative to the pressure of fluid in the input conduit, the fluid is directed through an interactive region and exits the first fluid oscillator through an exhaust conduit. A coupling unit couples the output of the first fluid oscillator to the input conduit of the successive fluid oscillator, so that the expansion and contraction of the capacitance chambers occurs successively without the need for valves and/or complicated control circuitry, such as solenoids and cams. A return conduit at the last fluid oscillator returns the fluid to a second control conduit of the first fluid oscillator to refill the first capacitance chamber.

16 Claims, 5 Drawing Sheets

VALVE-LESS FLUID CONTROL CIRCUIT FOR RHYTHMIC ACTION DEVICES

BACKGROUND OF THE INVENTION

1. Field of the Invention

The present invention relates to mechanical devices providing rhythmic action. More particularly, the invention relates to fluid control circuits providing rhythmic action for sequential compression devices, such as circulatory assist devices.

2. Description of the Related Art

Various examples of fluid control circuits for sequential compression devices used to assist patients in circulating fluid around a limb or limbs are provided by U.S. Pat. Nos. 4,396,010 (to Arkans), 4,481,937 (to Arkans) and U.S. Pat. No. 4,858,596 (to Kolstedt). The contents of these patents are incorporated by reference herein as background material.

Prior art fluid control circuits utilize a series of valves and pressure relief valves, which must be periodically opened and closed, for circulating the liquid through a sleeve or cuff. Opening and closing of the valves requires either a series of solenoid controls (with sophisticated electronic controls) or cam actuators. The hardware necessary for the control of opening and closing valves uses large amounts of power and increases the bulk of such devices.

In addition, the mechanical action of the valves, solenoids and cams are prone to wear and tear, which will degrade the quality of the compression device over time, requiring high costs for maintenance and repair. Thus, there exists a need in the art for improvement in fluid control circuits.

One of the present inventors previously designed a valve-less artificial heart utilizing a dual fluid oscillator (U.S. Pat. No. 3,599,244, the content of which is incorporated by reference herein as background material), which relies on the dynamic flow properties of blood for its operation. In this device, the system provides better reliability than prior art artificial hearts using mechanical valves, which often fail.

However, the dual fluid oscillator of the prior art requires the placement of a pump at each output having a pressure, which is directly related to the input pressure, and is inversely related to the pressure head against which it is being pumped. Moreover, the fluid from one part of the dual fluid oscillator does not directly transfer the fluid to the second (or any other) oscillator, as would be required in a sequential compression device.

Finally, the prior art dual fluid oscillator also requires that the oscillator portions must be arranged contiguously with each other so that a filling of a first fluid oscillator with a working fluid increases the pressure to such a level that the pressure against a common diaphragm causes the diaphragm to press against the second fluid oscillator, emptying the second fluid oscillator.

SUMMARY OF THE INVENTION

Accordingly, it is an object of the present invention to develop a fluid control circuit having a plurality of fluid oscillators which can circulate the working fluid successively to each particular fluid oscillator without requiring the opening and closing of a series of valves.

To this end, according to the present invention, there is provided a valve-less fluid control circuit for controlling rhythmic action devices, such as circulatory assist devices. The fluid control circuit has a plurality of pressure sensitive fluid oscillators for circulating a fluid. Each fluid oscillator includes a capacitance chamber unit for peristaltic pumping of fluid after being filled via an input conduit and a resistance conduit. A first control conduit provides an outlet of fluid from the capacitance unit during peristaltic pumping, and when the pressure of the fluid in the first control conduit reaches a certain level relative to the pressure of fluid in the input conduit, the fluid is directed through an interactive region and exits the first fluid oscillator through an exhaust conduit. A coupling unit couples the output of the first fluid oscillator to the input conduit of the successive fluid oscillator, so that the expansion and contraction of the capacitance chambers occurs successively without the need for valves and/or complicated control circuitry, such as solenoids and cams. A return conduit at the last fluid oscillator returns the fluid to a second control conduit of the first fluid oscillator to refill the first capacitance chamber.

More particularly, the present invention is directed to a fluid control circuit for controlling rhythmic action devices, the fluid control circuit comprising a plurality of pressure sensitive fluid oscillators coupled together in a ring configuration for circulating a fluid, wherein each of the fluid oscillators comprises: an input conduit having a first end for receiving a working fluid; an interactive region communicating with a second end of the input conduit; a resistance conduit having a first end communicating with the interactive region; capacitance chamber means for storing the working fluid and for providing a peristaltic pumping of the working fluid, the capacitance chamber means communicating with a second end of the resistance conduit; an exhaust conduit communicating with the interactive region; a first control conduit for controlling a direction of the flow of the working fluid entering the interactive region, the first control conduit communicating at a first end with the capacitance chamber means and at a second end with the interactive region, so as to provide an output path of the working fluid pumped from the capacitance chamber means, the first control conduit communicating with the interactive region at an angle relative to the input conduit so that when a fluid pressure of the working fluid in the first control conduit reaches a certain predetermined level relative to the fluid pressure in the input conduit, the first control conduit controls a flow direction of the working fluid entering the interactive region from the input conduit, so as to direct the flow toward the exhaust conduit; and wherein the fluid control circuit further comprises coupling means for coupling the plurality of fluid oscillators together so that an output from the exhaust conduit of each fluid oscillator is coupled to the input conduit of a successive one of the fluid oscillators in the ring configuration, so that the working fluid circulates successively through the respective capacitance chambers of the fluid control circuit without valves.

The first fluid oscillator of the plurality of fluid oscillators may further comprise a second control conduit communicating with the interactive region at an angle relative to the input conduit, so that when a fluid pressure of the working fluid in the second control conduit reaches a certain predetermined level relative to the fluid pressure in the input conduit, the second control conduit controls the direction of the working fluid to flow towards the capacitance chamber means; and a last fluid oscillator of the plurality of oscillators may comprise a return conduit having a first end communicating with the exhaust conduit of the last fluid oscillator, and a second end communicating with the second control conduit of the first fluid oscillator, so that at least a portion of the working fluid exiting the last oscillator is recirculated to the first fluid oscillator from the return conduit to the second control conduit, so as to control the direction of the fluid to flow towards the capacitance chamber means.

The capacitance chamber means of the plurality of fluid oscillators may include expandable sleeves which successively expand and contract as the working fluid is circulated successively through each of the plurality of fluid oscillators.

The device means for coupling may include venting means arranged between the exhaust conduit of one of the fluid oscillators and the input conduit of a successive one of the fluid oscillators.

At least one of the fluid oscillators may comprise a valve-less booster pump arranged at one of (i) the input conduit, (ii) the coupling means, and (iii) the exhaust conduit or at least one fluid oscillator which comprises a centrifugal pump arranged at one of (i) the input conduit, (ii) the coupling means, and (iii) the exhaust conduit.

The device may further comprise pressure adjustment means for adjusting a working fluid pressure in at least one of the first conduit, the second conduit, and the return conduit. The pressure adjustment means may comprise a valve-less pump.

The device may further comprise temperature control means to heat and cool the fluid.

According to another aspect of the present invention, there is provided a circulatory assist device comprising a fluid control circuit for controlling rhythmic action devices, the fluid control circuit comprising a plurality of pressure sensitive fluid oscillators coupled together in a ring configuration for circulating a fluid, wherein each of the fluid oscillators comprises: an input conduit having a first end for receiving a working fluid; an interactive region communicating with a second end of the input conduit; a resistance conduit having a first end communicating with the interactive region; capacitance chamber means for storing the working fluid and for providing a peristaltic pumping of the working fluid, the capacitance chamber means communicating with a second end of the resistance conduit; an exhaust conduit communicating with the interactive region; a first control conduit for controlling a direction of the flow of the working fluid entering the interactive region, the first control conduit communicating at a first end with the capacitance chamber means and at a second end with the interactive region, so as to provide an output path of the working fluid pumped from the capacitance chamber means, the first control conduit communicating with the interactive region at an angle relative to the input conduit so that when a fluid pressure of the working fluid in the first control conduit reaches a certain predetermined level relative to the fluid pressure in the input conduit, the first control conduit controls a flow direction of the working fluid entering the interactive region from the input conduit, so as to direct the flow toward the exhaust conduit; and wherein the fluid control circuit further comprises coupling means for coupling the plurality of fluid oscillators together so that an output from the exhaust conduit of each fluid oscillator is coupled to the input conduit of a successive one of the fluid oscillators in the ring configuration, so that the working fluid circulates successively through the respective capacitance chambers of the fluid control circuit without valves, and wherein the capacitance chamber means of each of the fluid oscillators comprises expandable sleeve means for wrapping around at least a portion of a limb of a patient, and the sleeve means of the plurality of fluid oscillators are coupled to each other so that the sleeve means expand and contract successively in the plurality of fluid oscillators as the working fluid circulates through the fluid control circuit. The fluid in each of the expandable sleeve means may comprise air or a liquid.

The circulatory assist device may further comprise temperature control means to heat and cool the air or the liquid.

The circulatory assist device may further comprise pressure adjustment means for adjusting a fluid pressure in at least one of the first control conduit, the second control conduit, and the return conduit.

The circulatory assist device may further comprise line pressure sustaining means for sustaining line pressure in the fluid control circuit and comprising an auxiliary valve-less pumping compartment arranged between at least two of the fluid oscillators.

DETAILED DESCRIPTION OF THE PREFERRED EMBODIMENTS

An embodiment of the valve-less fluid control circuit of the present invention is shown in FIGS. 1 through 4.

Figure 1:
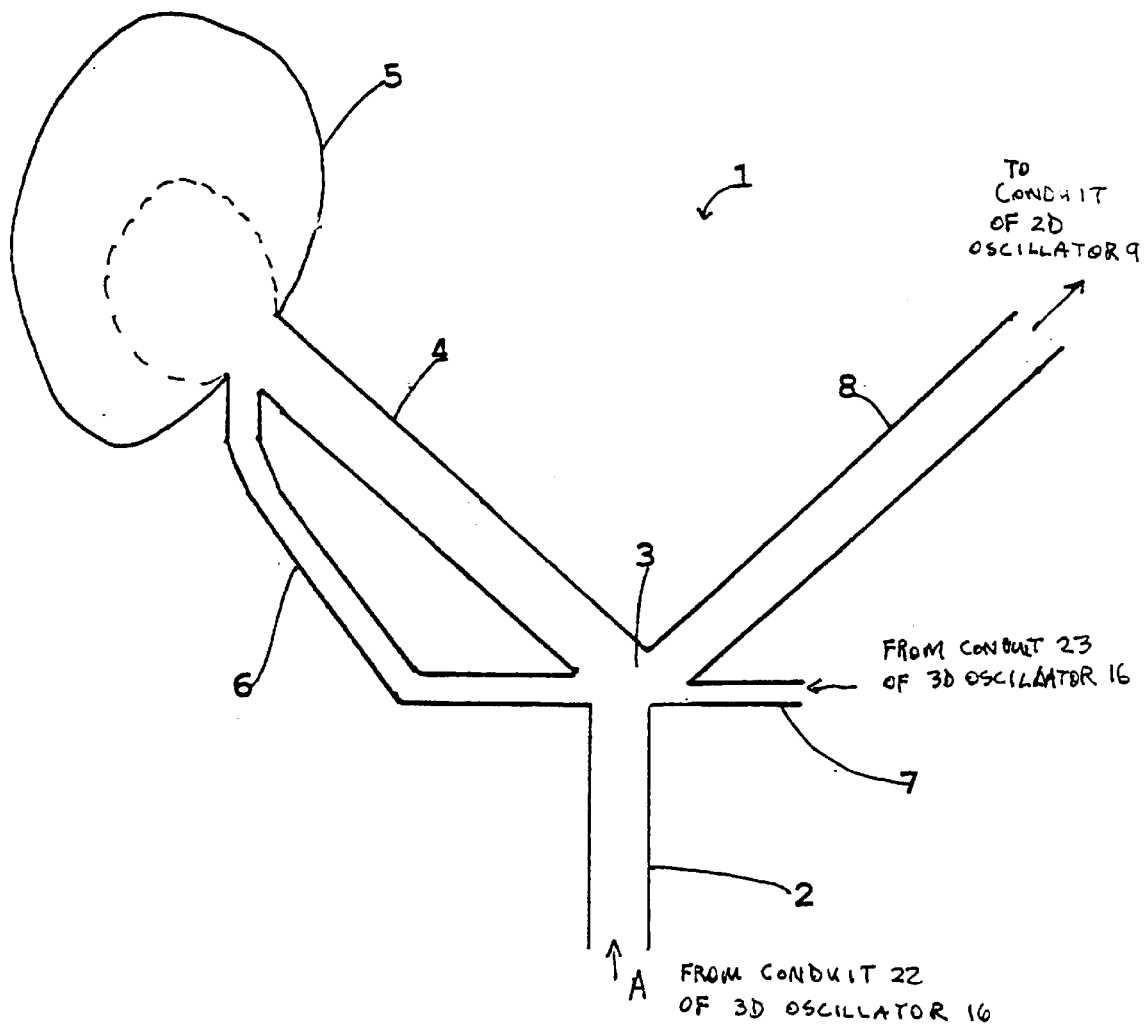
FIG. 1 shows a first fluid oscillator of the valve-less fluid control circuit according to the present invention.

In FIG. 1, a fluid control circuit includes a first fluid oscillator 1, a second fluid oscillator 9, a third (or last) fluid oscillator 16, and assorted coupling mechanisms 24, 25 for coupling the fluid oscillators together.

As shown in FIG. 1, first fluid oscillator 1 has an input conduit 2 which receives a working fluid (represented by arrow A) at a first end. Initially, if the working fluid is a liquid, a valve-less pump (not shown) may propel the working fluid into conduit 2. However, if the working fluid is air, a compressor (not shown) may be used instead of a pump. It is also within the scope of the invention that the working fluid may include a combination of liquid and air, requiring a suitable propulsion device.

The working fluid in input conduit 2 travels toward interactive region 3. Interactive region 3 is formed at the intersection of input conduit 2, resistance conduit 4, first control conduit 6, second control conduit 7, and exhaust conduit 8.

The interactive region 3 is formed so that the working fluid normally flows from input conduit 2 to interactive region 3, then to resistance conduit 4. The resistance conduit 4 is connected with a first pumping cuff 5, which comprises an expansive capacitance chamber which is expandable to a maximum size shown by the solid line and is represented in an empty or deflated state by the dashed line (not drawn to scale).

The first pumping cuff 5 is provided for two purposes. The first purpose is to provide the capacitance required to hold the working fluid. The second purpose is for providing a peristaltic pumping of the working fluid from the first fluid oscillator 1 into the second (or successive) fluid oscillator 9 without opening and closing of valves.

As the first pumping cuff 5 fills with working fluid, the chamber expands so as to begin the first stage of the peristaltic pumping. As the working fluid continues to enter the first pumping cuff 5, the pressure inside the pumping cuff continues to increase.

When the pressure of the working fluid inside the pumping cuff 5 reaches a certain level, it begins to exit the first pumping cuff 5 through the first control conduit 6, even as input fluid continues to enter the first pumping cuff 5 from the resistance conduit 4. The pressure of the working fluid passing through the first control conduit 6 is proportional to the pressure in the pumping cuff 5.

At a prescribed pressure, the working fluid in the first control conduit 6 will be sufficient to force the working fluid entering the interactive region 3 (from input conduit 2) to flow toward exhaust conduit 8.

When the working fluid is being directed away from the resistance conduit 4 and is not entering first pumping cuff 5, there is a contraction of the first pumping cuff 5 (part of the peristaltic process). The working fluid remaining in the pumping cuff is forced out by the contraction and flows toward the exhaust conduit 8. The exhaust conduit 8 is coupled to the input conduit of the second fluid oscillator 9.

Thus, the first fluid oscillator 1 of the fluid control circuit switches the flow of the working fluid without the use of any valves or solenoid mechanisms which would be required in the fluid control circuits of the prior art.

The second fluid oscillator 9 (FIG. 2) receives the working fluid by input conduit 10 connected to exhaust conduit of the first fluid oscillator 1. The working fluid flows toward interactive region 11 of second oscillator 9. The construction of the second fluid oscillator 9 is similar to the first fluid oscillator 1 in that the input fluid will flow towards the resistance conduit 12 and into the second pumping cuff 13 comprising a second expansive capacitance chamber.

The second pumping cuff 13 fills with fluid and begins to expand, which begins the second stage of the peristaltic pumping process.

Similar to the action in the first fluid oscillator 1, part of the working fluid in the second pumping cuff 13 begins to flow through first control conduit 14 at an increasing rate of pressure.

When the pressure of the working fluid flowing through first control conduit 14 reaches a certain magnitude, the working fluid entering the interactive region 11 (from input conduit 10) will be directed toward the exhaust conduit 15.

Thereafter, the second pumping cuff 13 contracts because there is no longer an input of working fluid into its chamber.

This contraction forces the remaining fluid out of the second pumping cuff toward the exhaust conduit 15.

The third fluid oscillator 16 (FIG. 3) is coupled to both the second fluid oscillator 9 to receive the working fluid and the first fluid oscillator 1 to begin a recirculation of the working fluid.

The input conduit 17 of the third fluid oscillator 16 is coupled to the exhaust conduit 15 of the second fluid oscillator 9 (coupling not shown), so that the fluid from the second fluid oscillator 9 enters the third fluid oscillator 16 and fills the third third pumping cuff 20 comprising a third expansive capacitance chamber via interactive region 18 and resistance conduit 19.

The third pumping cuff 20 begins to expand as it fills with working fluid, starting the third stage of the peristaltic pumping process.

The pressure of the working fluid flowing through first control conduit 21 begins to increase as the pressure of the fluid inside the third pumping cuff 20 increases.

Similar to the operation of the first and second fluid oscillators, the working fluid in the third fluid oscillator flowing from the first control conduit 21 to the interactive region 18 begins to divert the working fluid entering interactive region 18 (from input conduit 17) so that it flows toward exhaust conduit 22.

At this time, the third pumping cuff 20 contracts because the working fluid is no longer entering its chamber to retain the expanded condition, and the remaining working fluid in the third pumping cuff 20 is forced out towards the exhaust conduit 22.

The exhaust conduit 22 is coupled (coupling not shown) to the input conduit 2 of the first fluid oscillator, and a return conduit 23 is coupled (coupling not shown) to the second control conduit 7 of the first fluid oscillator 1.

Accordingly, the working fluid flowing from return conduit 23 to second control conduit 7 will force the fluid flowing from exhaust conduit 22 (into input conduit 2) to be directed to the first pumping cuff 5 via the resistance conduit 4. In this manner, the peristaltic pumping operation can be restarted.

Figure 4B:
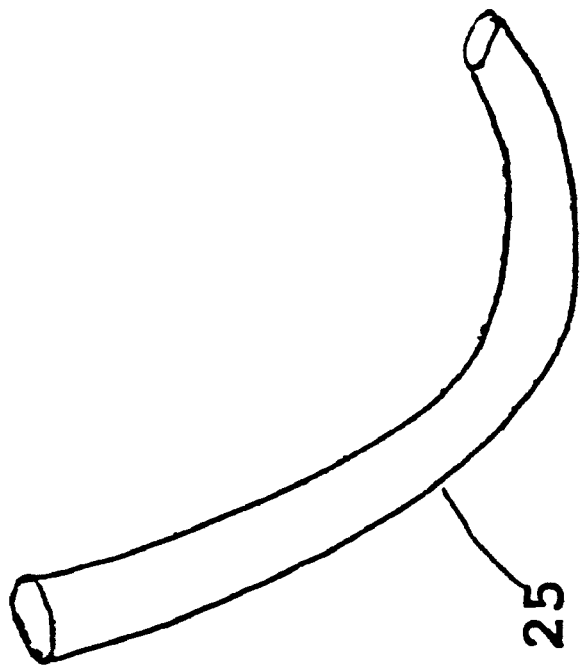
FIGS. 4(a)–4(c) illustrate several embodiments of a coupling unit for coupling together the fluid oscillators shown in FIGS. 1–3.
Figure 4A:
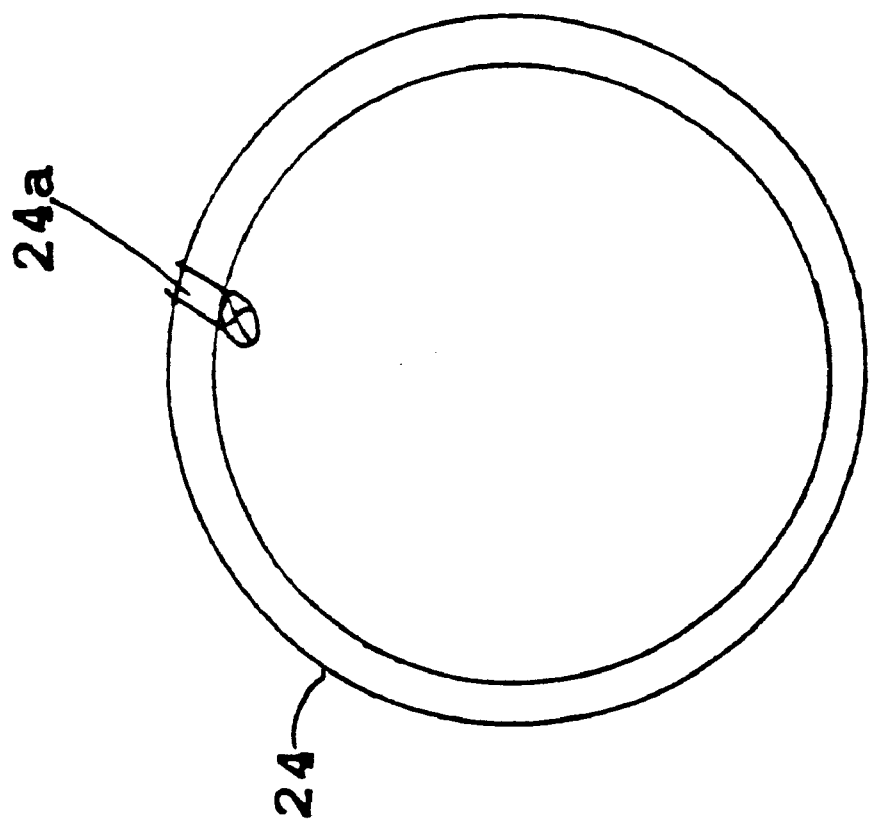
Figure 4C:
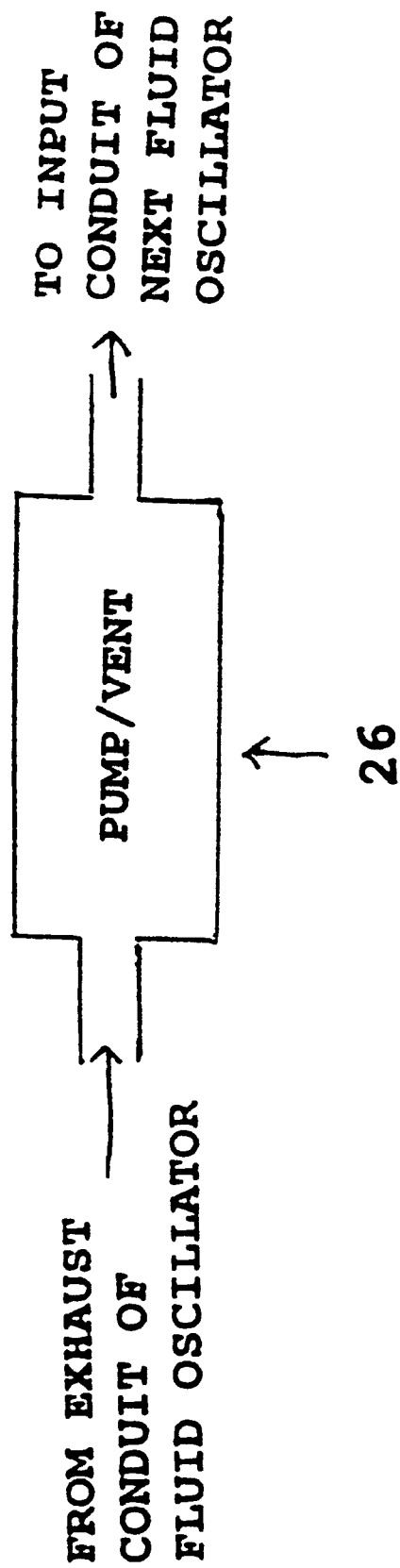

FIGS. 4(a)–(c) show three possible coupling units for the fluid control circuit of the present invention.

FIG. 4(a) illustrates a clamp 24 including a screw assembly 24a which may be used to connect the exhaust conduit of one fluid oscillator to the input conduit of a successive fluid oscillator.

FIG. 4(b) shows a sleeve 25 which would receive both the exhaust conduit of one fluid oscillator and the input conduit of a successive fluid oscillator.

FIG. 4(c) is a block diagram of a coupling device including a valve-less booster pump/vent 26 which may be used for coupling the output of one fluid oscillator to the input conduit of a successive fluid oscillator. The inline pressure may be sustained at a prescribed level by the booster pump. Additionally, venting of the fluid may be provided by a vent connected with the pump. Those of ordinary skill in the art would know that the actual arrangement of the venting within the fluid control circuit would be dependent upon a particular application of the invention.

One particular application of the above-described fluid control circuit is as a circulatory assist device, for example, for aiding a patient who is either bed-ridden or has a weak heart, whereby the pumping cuffs sequentially compress portions of a limb (or limbs) to prevent fluid retention. However, it will be understood by those of ordinary skill in the art that this invention has many applications and is not limited to circulatory assist devices.

The number of fluid oscillators in the fluid control circuit may be increased according as needed. It will be understood by those of ordinary skill in the art that variations and modifications of the arrangement of the conduits and their shape may be effected as necessary to suit a particular application.

Figure 2:
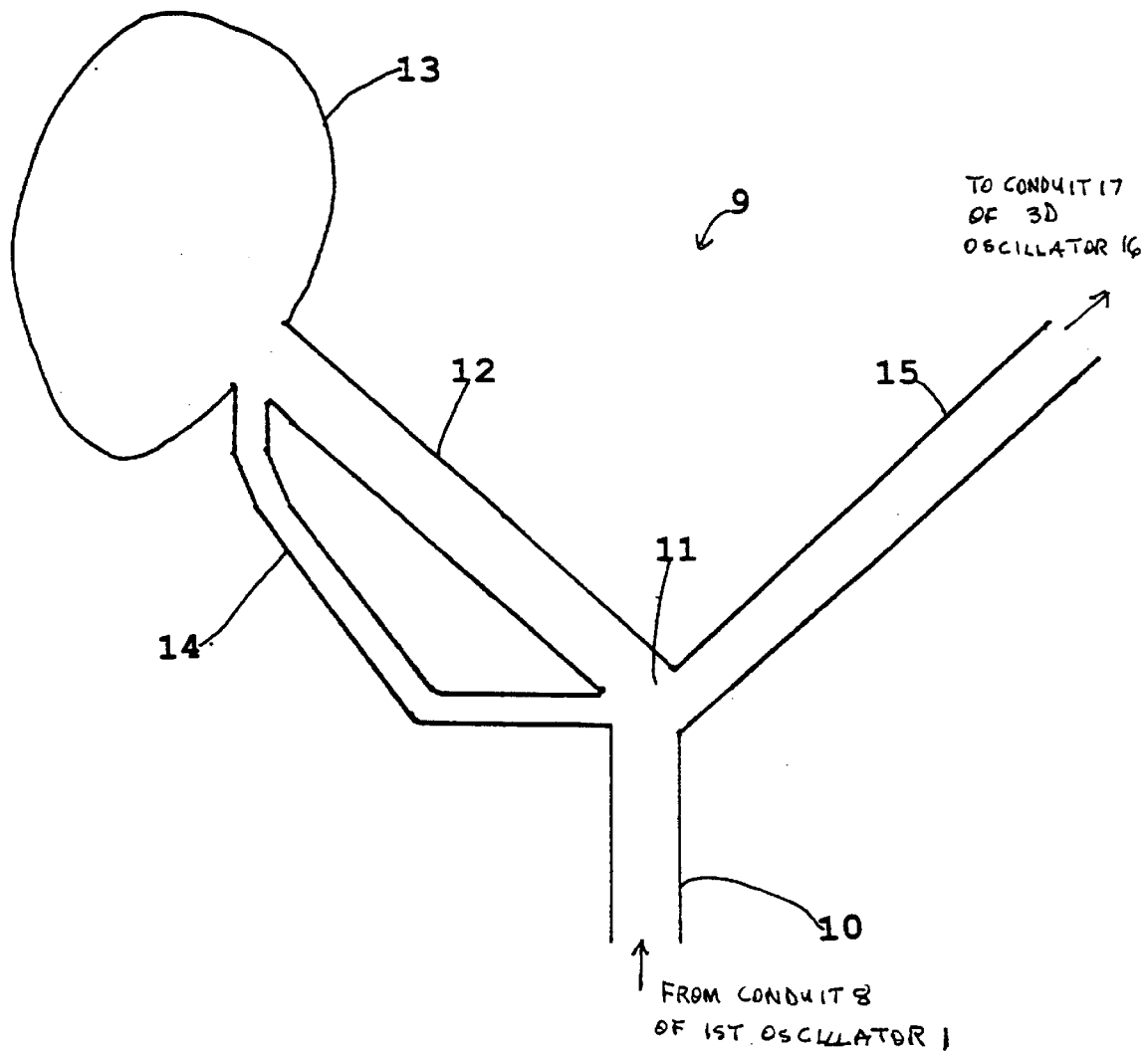
FIG. 2 illustrates a second or subsequent fluid oscillator of the valve-less fluid control circuit according to the present invention.
Figure 3:
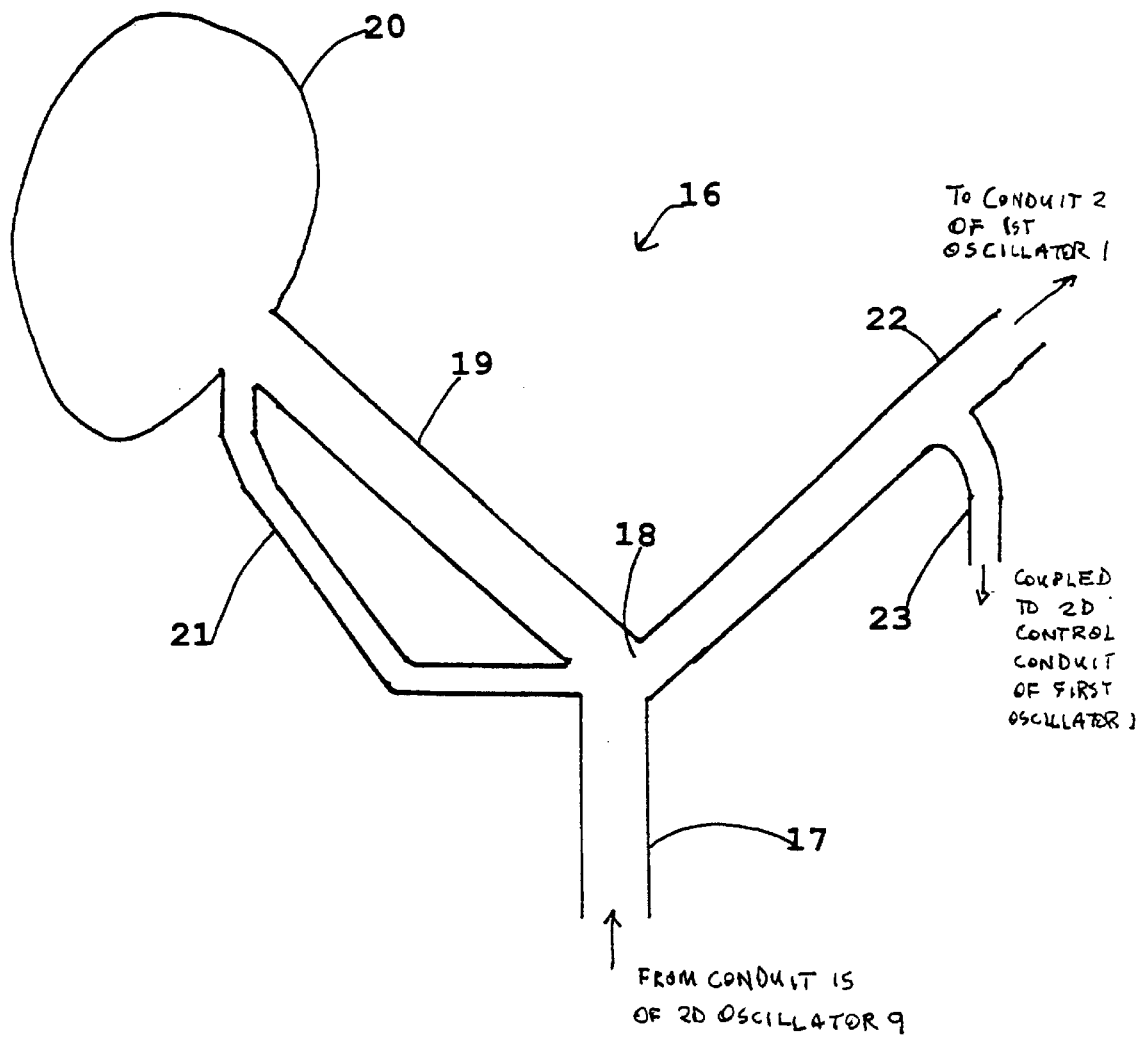
FIG. 3 illustrates a third or last fluid oscillator of the valve-less fluid control circuit according to the present invention.

It is also within the scope of the invention to use a combination of the coupling devices shown in FIGS. 2–4, as well as other coupling devices known in the art.

The first fluid oscillator 1 may include a valve-less booster pump 26 or a compressor (not shown) connected to the input conduit 2 in a multiple connection (such as a T-connection), so that the pump or compressor can begin the flow of the working fluid in the fluid control circuit from a reservoir portion. The T-connection allows the working fluid to enter the input conduit 2 of the first fluid oscillator 1 after circulating through the third (or last) fluid oscillator 16.

Although the present invention has been fully described by way of example with reference to the accompanying drawings, it should be understood that numerous variations, modifications and substitutions, as well as rearrangements and combinations, of the preceding embodiments will be apparent to those skilled in the art without departing from the novel spirit and scope of this invention, and the appended claims.

What is claimed is:

1. A fluid control circuit for controlling rhythmic action devices, said fluid control circuit comprising:

a plurality of pressure sensitive fluid oscillators coupled together in a ring configuration for circulating a fluid, wherein each of said fluid oscillators comprises:

an input conduit having a first end for receiving a working fluid;

an interactive region communicating with a second end of said input conduit;

a resistance conduit having a first end communicating with said interactive region;

capacitance chamber means for storing the working fluid and for providing a peristaltic pumping of the working fluid, said capacitance chamber means communicating with a second end of said resistance conduit;

an exhaust conduit communicating with said interactive region;

a first control conduit for controlling a direction of the flow of the working fluid entering said interactive region, said first control conduit communicating at a first end with said capacitance chamber means and at a second end with said interactive region, so as to provide an output path of the working fluid pumped from said capacitance chamber means, said first control conduit communicating with said interactive region at an angle relative to said input conduit so that when a fluid pressure of the working fluid in said first control conduit reaches a certain predetermined level relative to the fluid pressure in said input conduit, said first control conduit controls a flow direction of the working fluid entering said interactive region from said input conduit, so as to direct the flow toward said exhaust conduit; and wherein said fluid control circuit further comprises coupling means for coupling said plurality of fluid oscillators together so that an output from the exhaust conduit of each fluid oscillator is coupled to the input conduit of a successive one of said fluid oscillators in said ring configuration, so that the working fluid circulates successively through the respective capacitance chambers of said fluid control circuit without valves.

2. The device according to claim 1, wherein:

a first fluid oscillator of said plurality of fluid oscillators further comprises a second control conduit communicating with said interactive region at an angle relative to said input conduit, so that when a fluid pressure of the working fluid in said second control conduit reaches a certain predetermined level relative to the fluid pressure in said input conduit, said second control conduit controls the direction of the working fluid to flow towards said capacitance chamber means; and a last fluid oscillator of said plurality of oscillators comprises a return conduit having a first end communicating with the exhaust conduit of said last fluid oscillator, and a second end communicating with said second control conduit of said first fluid oscillator, so that at least a portion of the working fluid exiting said last oscillator is recirculated to said first fluid oscillator from said return conduit to said second control conduit, so as to control the direction of the fluid to flow towards said capacitance chamber means.

3. The device according to claim 1, wherein said capacitance chamber means of said plurality of fluid oscillators include expandable sleeves which successively expand and contract as the working fluid is circulated successively through each of said plurality of fluid oscillators.

4. The device according to claim 1, wherein said means for coupling includes venting means arranged between the exhaust conduit of one of said fluid oscillators and the input conduit of a successive one of said fluid oscillators.

5. The device according to claim 1, wherein at least one of said fluid oscillators comprises a valve-less booster pump arranged at one of (i) the input conduit, (ii) the coupling means, and (iii) the exhaust conduit.

6. The device according to claim 1, wherein at least one fluid oscillator comprises a centrifugal pump arranged at one of (i) the input conduit, (ii) the coupling means, and (iii) the exhaust conduit.

7. The device according to claim 1 further comprising pressure adjustment means for adjusting a working fluid pressure in at least one of said first conduit, said second conduit, and said return conduit.

8. The device according to claim 7 wherein said pressure adjustment means comprises a valve-less pump.

9. The device according to claim 1 further comprising temperature control means to heat and cool said fluid.

10. A circulatory assist device comprising a fluid control circuit for controlling rhythmic action devices, said fluid control circuit comprising a plurality of pressure sensitive fluid oscillators coupled together in a ring configuration for circulating a fluid, wherein each of said fluid oscillators comprises: an input conduit having a first end for receiving a working fluid; an interactive region communicating with a second end of said input conduit; a resistance conduit having a first end communicating with said interactive region; capacitance chamber means for storing the working fluid and for providing a peristaltic pumping of the working fluid, said capacitance chamber means communicating with a second end of said resistance conduit; an exhaust conduit communicating with said interactive region; a first control conduit for controlling a direction of the flow of the working fluid entering said interactive region, said first control conduit communicating at a first end with said capacitance chamber means and at a second end with said interactive region, so as to provide an output path of the working fluid pumped from said capacitance chamber means, said first control conduit communicating with said interactive region at an angle relative to said input conduit so that when a fluid pressure of the working fluid in said first control conduit reaches a certain predetermined level relative to the fluid pressure in said input conduit, said first control conduit controls a flow direction of the working fluid entering said interactive region from said input conduit, so as to direct the flow toward said exhaust conduit; and wherein said fluid control circuit further comprises coupling means for coupling said plurality of fluid oscillators together so that an output from the exhaust conduit of each fluid oscillator is coupled to the input conduit of a successive one of said fluid oscillators in said ring configuration, so that the working fluid circulates successively through the respective capacitance chambers of said fluid control circuit without valves, and wherein said capacitance chamber means of each of said fluid oscillators comprises expandable sleeve means for wrapping around at least a portion of a limb of a patient, and said sleeve means of said plurality of fluid oscillators are coupled to each other so that the sleeve means expand and contract successively in said plurality of fluid oscillators as the working fluid circulates through said fluid control circuit.

11. The circulatory assist device according to claim 10, wherein the fluid in each of said expandable sleeve means comprises air.

12. The circulatory assist device according to claim 10, wherein the fluid in each of said expandable sleeve means comprises a liquid.

13. The circulatory assist device according to claim 11, further comprising temperature control means to heat and cool said air.

14. The circulatory assist device according to claim 12, further comprising temperature control means to heat and cool said liquid.

15. The circulatory assist device according to claim 10, further comprising pressure adjustment means for adjusting a fluid pressure in at least one of said first control conduit, said second control conduit, and said return conduit.

16. The circulatory assist device according to claim 12, further comprising line pressure sustaining means for sustaining line pressure in said fluid control circuit and comprising an auxiliary valve-less pumping compartment arranged between at least two of said fluid oscillators.

* * * * *